(12) United States Patent
Cuffe et al.

(10) Patent No.: US 7,389,692 B2
(45) Date of Patent: Jun. 24, 2008

(54) DIGITAL LOG AMPLIFIER FOR ULTRASONIC TESTING

(75) Inventors: John Michael Cuffe, Reedsville, PA (US); Klaus-Peter Busch, Rodenbach (DE); Scott Allen Herbster, Middleburg, PA (US)

(73) Assignee: GE Inspection Technologies, LP, Lewistown, PA (US)

( * ) Notice: Subject to any disclaimer, the term of this patent is extended or adjusted under 35 U.S.C. 154(b) by 370 days.

(21) Appl. No.: 11/266,854

(22) Filed: Nov. 4, 2005

(65) Prior Publication Data

US 2007/0101816 A1   May 10, 2007

(51) Int. Cl.
  *G01N 29/06* (2006.01)
  *G01N 29/44* (2006.01)
  *A61B 8/08* (2006.01)
  *A61B 8/00* (2006.01)
(52) U.S. Cl. .................. 73/602; 600/437; 600/443
(58) Field of Classification Search ............... 73/602
  See application file for complete search history.

(56) References Cited

U.S. PATENT DOCUMENTS

| 4,099,416 A | 7/1978 | Niklas |
| 4,240,281 A | 12/1980 | Lather et al. |
| 4,283,952 A | 8/1981 | Newman |
| 4,391,124 A | 7/1983 | Drost et al. |
| 4,434,648 A | 3/1984 | Drost et al. |
| 4,462,082 A | 7/1984 | Thiele et al. |
| 4,545,251 A | 10/1985 | Uchida et al. |
| 4,649,750 A | 3/1987 | Cantrell, Jr. et al. |
| 4,652,882 A | 3/1987 | Shovlin et al. |
| 4,788,981 A | 12/1988 | Nagasaki et al. |
| 4,799,177 A | 1/1989 | Sarr |
| 5,373,741 A * | 12/1994 | Volkmann et al. ............ 73/602 |
| 5,596,508 A | 1/1997 | Cuffe |
| 5,929,315 A | 7/1999 | Dunegan |
| 6,016,700 A | 1/2000 | Cuffe |

(Continued)

FOREIGN PATENT DOCUMENTS

| JP | 57131058 A | 8/1982 |
| JP | 59013953 A | 1/1984 |
| JP | 7-263990 A | 10/1995 |

*Primary Examiner*—Hezron Williams
*Assistant Examiner*—Rose M Miller
(74) *Attorney, Agent, or Firm*—Marjama Muldoon Blasiak & Sullivan LLC

(57) ABSTRACT

The apparatus and method of the present invention provides a plurality of linear amplifiers simultaneously processing an ultrasonic signal. Each amplifier of the plurality of linear amplifiers has a predetermined gain level suitable for achieving the desired output signal level for input to an analog to digital (A/D) converter for processing. The output of each amplifier is sampled by each respective A/D converter at a very high frequency to convert the analog signal output of each of the linear amplifiers to a digital signal. Logic circuits simultaneously monitor all of the output digital signals from the A/D converters. The logic circuits determine which output of the A/D converters has the greatest linear output and stores the selected output in a memory storage device. The saved output waveforms are subsequently combined into a continuous linear digital output that has a dynamic response range that is approximately the sum of the individual dynamic response ranges of the individual amplifiers and A/D converters. The combined continuous linear digital output waveform may be input to a logarithmic conversion to produce a waveform having a wide dynamic range.

22 Claims, 3 Drawing Sheets

U.S. PATENT DOCUMENTS

| | | |
|---|---|---|
| 6,031,478 A | 2/2000 | Oberhammer et al. |
| 6,063,033 A * | 5/2000 | Haider et al. ............... 600/447 |
| 6,142,942 A | 11/2000 | Clark |
| 6,263,094 B1 | 7/2001 | Rosich et al. |
| 6,343,513 B1 | 2/2002 | Yost et al. |
| 6,932,770 B2 * | 8/2005 | Hastings et al. ............. 600/443 |
| 6,997,875 B2 * | 2/2006 | Brock-Fisher et al. ...... 600/443 |
| 2004/0059218 A1 * | 3/2004 | Kanda et al. ................ 600/437 |

* cited by examiner

DIGITAL LOG AMPLIFIER FOR ULTRASONIC TESTING

FIELD OF THE INVENTION

The present invention is directed to a method and system for processing acoustic signals for use in ultrasonic inspection and testing, and more particularly to simultaneously processing an acoustic signal with multiple linear amplifiers to obtain a combined linear digital output signal having a dynamic response range that is greater than the individual ranges of the amplifiers.

BACKGROUND OF THE INVENTION

Ultrasonic inspection employs high frequency, ultrasonic waves generated by a transducer to examine test objects and make measurements. Ultrasonic inspection can be used for detection of flaws in test objects, and for performing evaluation, dimensional measurements, material characterization, and more on objects. Measurement procedures initially developed for metals have been extended to engineered materials such as composites, where such characteristics as anisotropy and inhomogeneity are of concern. Advances in digitization and computing capabilities have changed the types of instruments and algorithms that are used in processing the resulting data. High-resolution imaging systems and multiple measurement modalities for characterizing a flaw have emerged. Of interest are detecting, characterizing, and sizing defects, as well as characterizing the materials in which they are found. The objectives of ultrasonic testing range from the determination of fundamental microstructural characteristics such as grain size, porosity, texture and preferred grain orientation, to material properties related to failure mechanisms such as fatigue, creep, and fracture toughness.

In ultrasonic testing, a transducer containing a piezoelectric element is excited by an electrical pulse to transmit an ultrasonic pulse into a test object. The sound wave propagates through the test object and is reflected. The transducer receives the reflected wave and the reflected wave is converted by the transducer into an electrical signal and analyzed to determine whether a discontinuity exists in the test object. A flaw or discontinuity in the test object is characterized by certain anomalous profiles in the electrical signal that are viewable on an analog display, such as an oscilloscope or a recording device.

The electrical signal from a transducer representing the reflected sound wave must be amplified for input into a display or recording device. In order to be displayed, the amplified signal must fall within a certain dynamic response range that is defined by the maximum and minimum operating parameters of the respective display device. In many cases, the signal representing the acoustic wave includes multiple components. For example, in the case of a flaw occurring near the surface of an object, the echo caused by the near-surface defect is received within the interval of the initial pulse. In that case the flaw is not detectable by a visual display, or a recording device, since the amplitude of the echo is small relative to the initial pulse. Since the instrument receives them concurrently, the relatively small-magnitude echo signal from the near-surface flaw is essentially superimposed on the larger initial pulse or interface signal. The large difference in amplitude of the two simultaneous signals makes the smaller signal very difficult to detect.

Previously, analog logarithmic amplifiers have been used in attempts to compress the dynamic response range, but analog amplifiers are not particularly well suited to perform this due to the limited bandwidth and dynamic response range of analog logarithmic amplifiers. Analog techniques are limited by noise and accuracy problems.

Therefore there is a need for a device for digitally processing simultaneous ultrasonic signals having widely varying amplitudes and combining them for display into a continuous linear digital signal having a wide dynamic range.

SUMMARY OF THE INVENTION

The apparatus and method of the present invention provides a plurality of linear amplifiers simultaneously processing an ultrasonic signal. Each amplifier of the plurality of linear amplifiers has a predetermined gain level suitable for achieving the desired output signal level for input to an analog to digital (A/D) converter for processing. The output of each amplifier is sampled by each respective A/D converter at a very high frequency to convert the analog signal output of each of the linear amplifiers to a digital signal. Logic circuits simultaneously monitor all of the output digital signals from the A/D converters. The logic circuits determine which output of the A/D converters has the greatest linear output and stores the selected output in a memory storage device. The saved output waveforms are subsequently combined into a continuous linear digital output that has a dynamic response range that is approximately the sum of the individual dynamic response ranges of the individual A/D converters. The combined continuous linear digital output waveform may be accurately converted by corresponding computing to logarithmic scaling to produce a waveform having a wide dynamic range comparable to the output of a logarithmic amplifier.

An advantage object of the present invention is that the device can detect small defects near the surface of a test object by eliminating the constant wave signal reflected from the top surface of the test object and detecting the small signals that are normally masked by the constant wave signal reflected from the top surface.

Another advantage of the present invention is that simultaneous reflected waveforms can be measured and recorded having a wide dynamic response range with no distortion of the respective waveforms.

Yet another advantage of the present invention is that a wide dynamic response range is provided for the measurement of signals reflected from various depths in a material characterized by high signal attenuation.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible the same reference numbers will be used throughout the drawings to refer to the same or like parts.

DETAILED DESCRIPTION OF THE INVENTION

Figure 1:
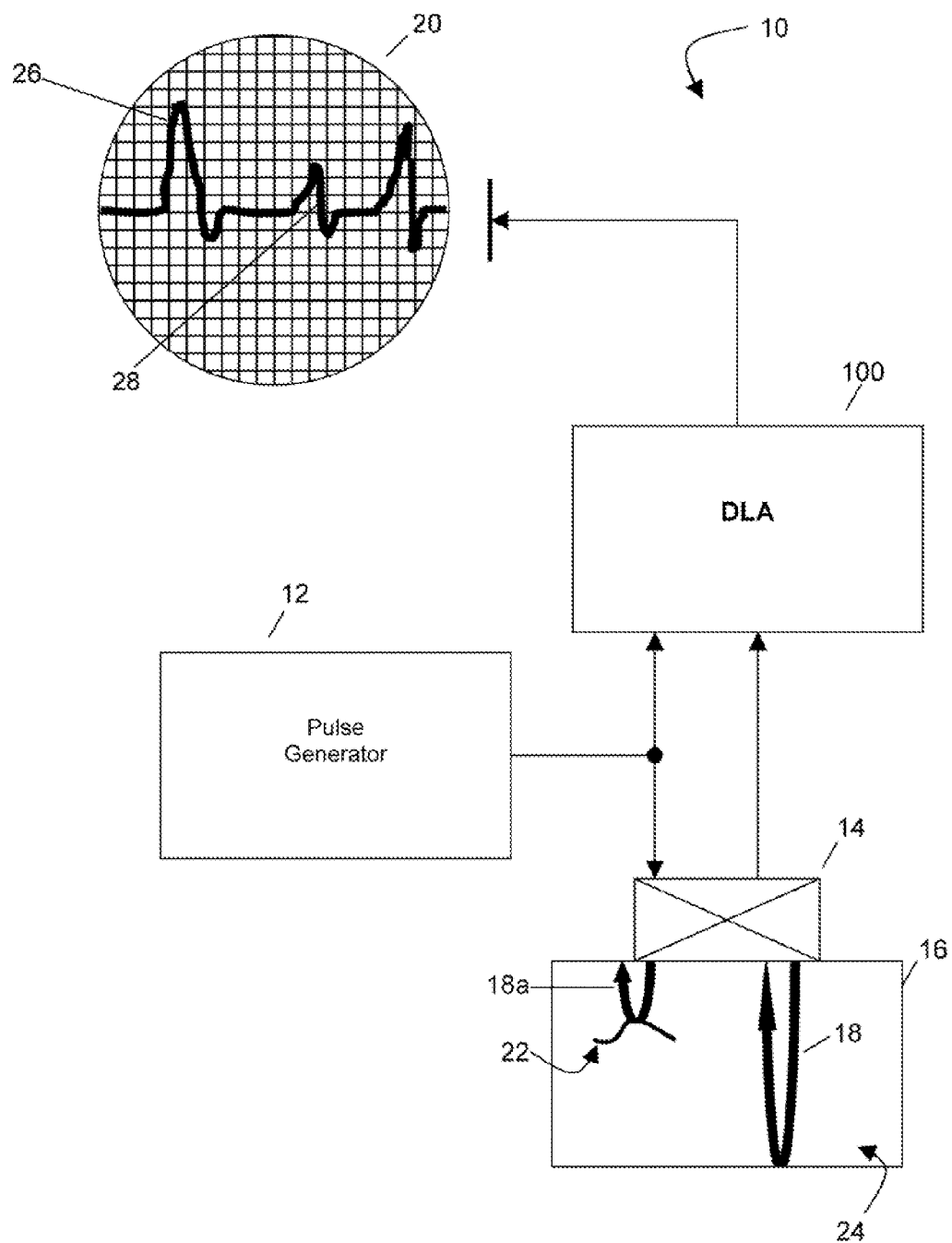
FIG. 1 is a schematic diagram of a test arrangement using the digital log amplifier of the present invention.

Referring to FIG. 1, a test inspection arrangement 10 includes a pulse generator circuit 12 that transmits a pulse to a transducer 14 for propagating an ultrasonic acoustic wave 18 through a test object 16. Wave 18 is reflected back to the transducer 14. In the example shown in FIG. 1, one transducer both transmits and receives the acoustic wave, however, other test configurations may also be employed with multiple transducers, some that transmit, some that receive, and some that perform both transmitting and receiving functions. The transducer 14 receives the reflected acoustic wave and converts it back into an electrical signal, which is input to the digital log amplifier (DLA) 100 of the present invention. The DLA 100 processes the electrical signal representing the reflected waveform, as discussed in further detail below. The output waveform of the DLA 100 is displayed on an oscilloscope 20 or other similar peripheral display or storage device (not shown). Many other test arrangements may be substituted for the arrangement of FIG. 1, as are well known to those skilled in the art. The arrangement of FIG. 1 is therefore presented as an example, and the invention is not limited to the particular arrangement of this example.

As indicated in FIG. 1, a defect 22 in the test object 16 will reflect the waveform 18 at a point different from a backwall 24 of the test object 16, resulting in different wave propagation times that may be shown on the screen of the oscilloscope 20. The smaller the defect 22, the smaller the magnitude of the reflected wave, so that in some instances, the sensitivity of the output device or the non-linearity of the amplifier, may cause a small reflected signal to be lost. Also, where the defect 22 is very near to the surface, the reflected wave 28 associated with the defect 22 may be received by the amplifier and output to the display 20 at approximately the same time as the initial pulse 26 or the interface signal. When displayed on an analog display the initial pulse 26 is very large in relation to the near-surface reflected wave 28, the small reflected signal 28 is also lost in the larger waveform.

Figure 2:
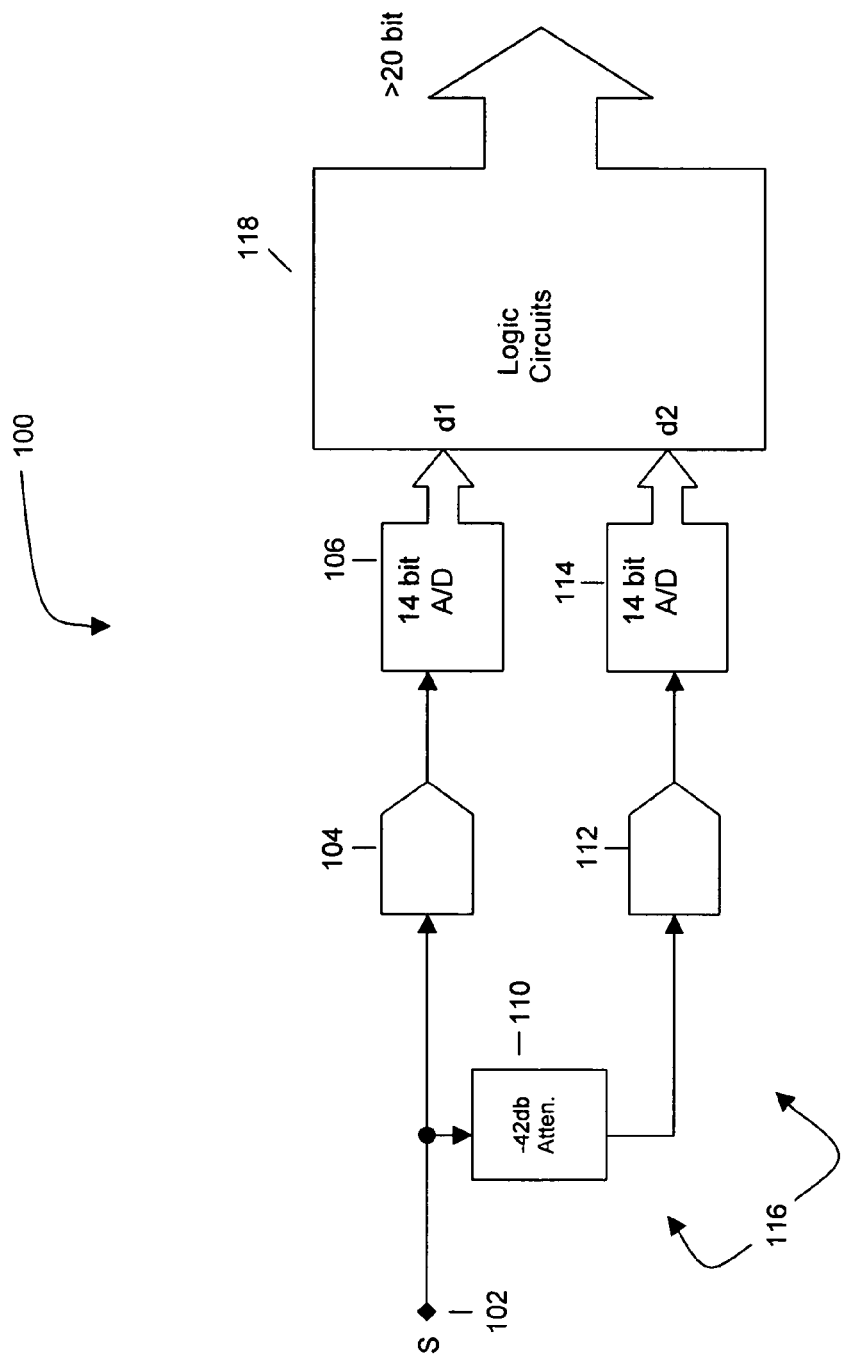
FIG. 2 is a schematic diagram of the digital log amplifier.

Referring to FIG. 2, signal S representing a reflected waveform propagated through a test object is applied to the input 102 of the DLA 100. An amplifier 104 has a gain suitable for processing the unattenuated signal S, and amplifies the signal S for input to an analog-to-digital (A/D) converter 106. Preferably, all of the A/D converters used in the present invention are 14-bit converters with a high-dynamic response range but the invention can principally perform on each type of analog to digital (A/D) converter. The output of amplifier 104 is inserted into the A/D converter 106 and sampled at a very high rate, to provide a digitized representation, $d_1$, of the analog signal S. The sampling frequency must be at least twice that of the analog signal frequency, and preferably in practice should be at least three times the frequency of analog signal S. The preferred sampling frequency for low signal frequency applications is around 50 MHz and for high signal frequency applications is around 100 MHz, but may be more or less depending on the frequency of the analog signal S.

Analog signal S is simultaneously processed by at least one attenuators. FIG. 2 illustrates only one attenuation path 116, but it is understood that the DLA 100 of the present invention may typically include multiple parallel paths with different attenuation values. Each attenuation path 116 includes an attenuator 110, an amplifier 112 and an A/D converter 114 connected in series, similar to attenuation path 116. In the example of FIG. 2, attenuator 110 attenuates signal S for input to amplifier 112. Attenuation values are preferably selected in increments of −6 db (e.g., −24 db, −30 db, −36 db, et. seq.), which conveniently correspond to an additional sampling bit for every 6 db of attenuation, however any magnitude of signal attenuation may be substituted if desired. In the example shown in FIG. 2, minus (−) 42 db signal attenuation is provided by the attenuator 110 before amplification. Amplifier 112 has a gain suitable for the dynamic response range of the attenuated signal S for providing a desired output level of the amplified signal. The output of the amplifier 112 is inserted into A/D converter 114 and simultaneously sampled at the same rate as A/D converter 106 to provide a second digitized representation, $d_2$, of the signal S. Any number of attenuator paths may be used to process signal S simultaneously for input to a corresponding number of amplifiers. Attenuation values are selectively assigned to match desired response levels, and each amplifier has a gain level designed with respect to the associated attenuator to provide the desired output signal level for the associated A/D converter.

Logic circuits 118 analyze the signal levels of the digitized outputs d1, d2 of the A/D converters 106, 114 or if additional paths are used the digitized outputs of all paths. The logic circuits 118 determine which of the converters 106, 114 has the greatest output, which is linear, as the amplitude of signal S fluctuates. The logic circuits 118 determine whether the digitized output signal from each converter falls between a predetermined saturation threshold and a predetermined minimum signal level. Those outputs falling outside the desired band are eliminated—i.e., outputs above the predetermined saturation level or below the minimum signal level. The selected converter output waveforms that fall between the saturation threshold and minimum levels are saved to a digital memory storage device (not shown). The saved output waveforms of signals with different amplitudes are subsequently combined by logic circuits 18 to form a continuous linear digital output for display on an oscilloscope 20 or other peripheral device connected to the amplifier output. At each sample point, $N_1$, $N_2$, $N_3$ etc., which occur every 20 nanoseconds at 50 MHz sample rate, the outputs from multiple A/D converters are available. Thus for sample point $N_1$, logic circuits 18 decide which output is within range and this amplitude is used in the logic circuit output. Next for sample point $N_2$, logic circuits 18 decide which A/D output to use in the logic circuit output. This process is continued for each sample point. Every 6 dB of attenuation (approximately) at the input to the 14-bit A/D converter 114 corresponds to an extra bit of sensitivity and a doubling of response range of the resulting logic circuit output signal. The dynamic response range of the resulting logic circuit output signal is greater than 20-bit, which corresponds with the sum of the multiple dynamic response ranges of individual amplifier and A/D converter combinations. The digitized signal may be converted to a logarithmic scaling by a corresponding conversion algorithm implemented in the logic circuits 18 for compressing the dynamic response range of the combined output signal to a screen or recorder presentation. This conversion algorithm produces logarithmic output that is more accurate over a greater dynamic range than can be produced by existing techniques.

Figure 3:
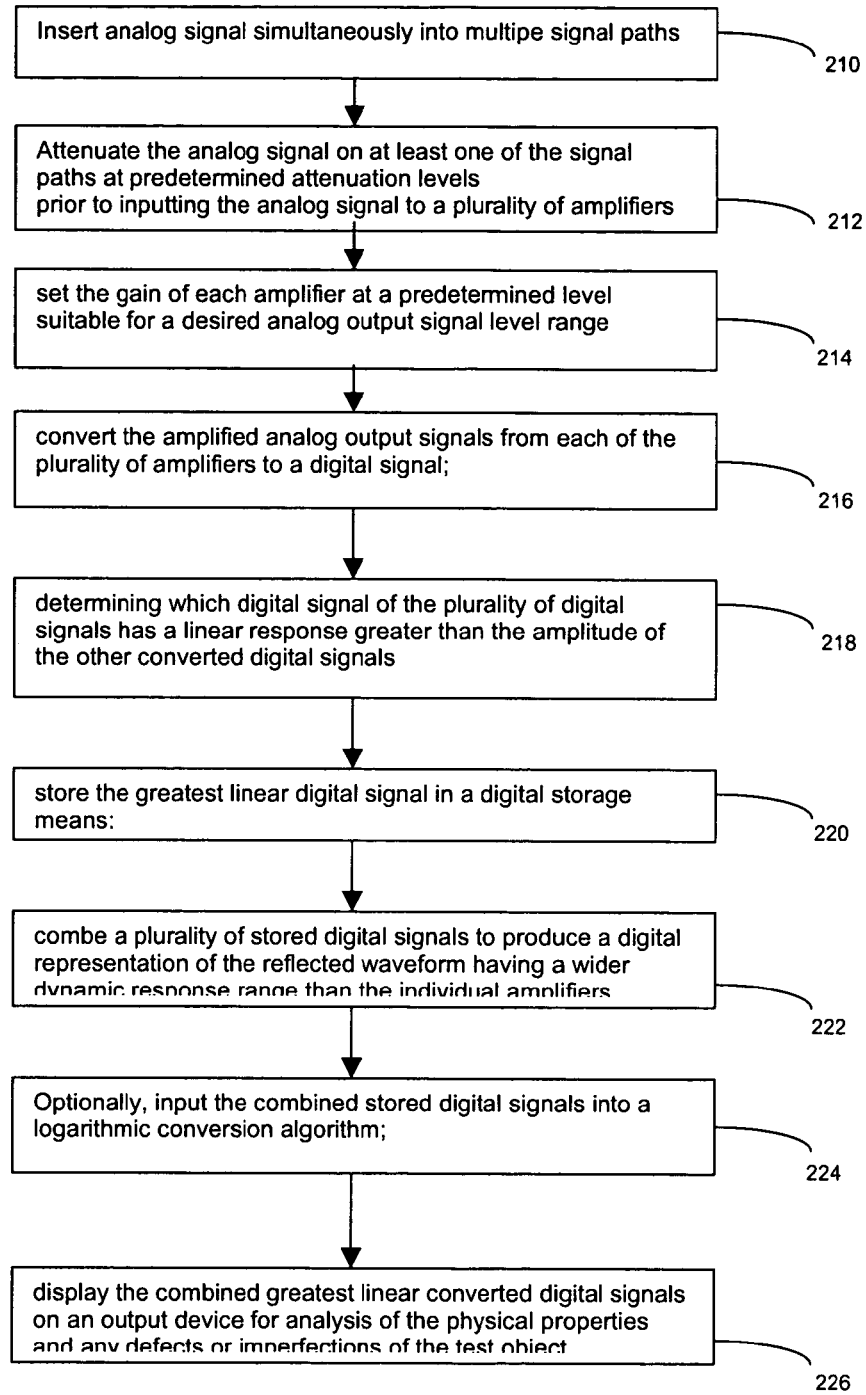
FIG. 3 is a flow chart of the method of converting an analog signal into a plurality of digital components representing a reflected ultrasonic waveform.

The method, for converting an analog signal into a plurality of digital components representing a reflected ultrasonic waveform for testing objects, is set forth in FIG. 3. The flowchart, generally designated 200, begins at step 210, processing a reflected analog signal by amplifying the analog signal simultaneously through a plurality of different amplifiers. Then, at step 212, the analog signal is attenuated at a plurality of predetermined attenuation levels prior to inputting the analog signal to at least one of the plurality of amplifiers. Next, at step 214, the gain of each of the plurality of amplifiers is set at a predetermined level suitable for a desired predetermined analog output signal level range. At step 216, the amplified analog output signals from each of the plurality of amplifiers are converted to a digital signal. Then, at step 218, the system determines which converted digital signal has a response that is (1) linear and (2) greater than the amplitude of the other converted digital signals. Following step 218, at step 220, that greatest linear converted digital signal is stored in memory or other digital storage means. Then at step 222 a plurality of the stored converted digital signals is combined to produce a digital representation of the reflected waveform, the digital representation of the reflected waveform has a wider dynamic response range than the response range of the separate individual amplifiers. At step 224, which is optional, the combined stored greatest linear converted digital signals is input to a logarithmic conversion algorithm. Then, at step 226, the combined greatest linear converted digital signals are displayed on an output device for analysis of the physical properties and any defects or imperfections of the test object.

It is known that small defects present near the surface of a test object are difficult to detect. The reflected waveform from the near-surface defect is very small, relative to the interface signal or surface reflection. The magnitude of the interface signal may be on the order of one hundred times the magnitude of the signal from the defect. Thus the larger signal overloads the amplifier, and the signal from the defect is contained within the larger waveform signal and is lost or undetectable. The interface may be subtracted from the amplifier output, since the magnitude and waveform of the interface signal is known. By eliminating the interface signal, smaller signals such as the near-surface flaw are selectively displayed, allowing the tester to obtain more accurate inspection results of near-surface defects. Also, where ultrasonic inspection techniques are employed to measure thickness of a test object, wide variations in amplitude may be eliminated by capturing the waveforms over a wide dynamic response range, allowing greater accuracy in thickness measurements.

Another advantage of the present invention is realized in the ultrasonic inspection of composite components which are characterized by high attenuation. The wide dynamic response range of the DLA permits accurate amplitude measurements of signals from various depths in test objects of composite materials, as well as testing composite objects with wide variations in thickness.

Finally, the DLA allows the combined outputs of the stored waveforms to be easily processed into logarithmic scaling without the noise and accuracy limitations normally associated with the analog logarithmic amplifiers.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. Apparatus for measuring physical properties of a test object using ultrasonic inspection techniques comprising:
    a pulse generator to generate an electrical pulse having predetermined characteristics;
    an ultrasonic wave generator, the ultrasonic wave generator receiving the electrical pulse from the pulse generator; the ultrasonic wave generator being configured to convert the electrical pulse to an ultrasonic wave and propagate the ultrasonic wave at an object, the ultrasonic wave generator being configured to receive a reflected ultrasonic wave from a test object and convert the reflected ultrasonic wave to an analog signal;
    a digital log amplifier for processing the analog signal comprising:
        at least one unattenuated processing path, each unattenuated processing path including amplifier means for amplifying the analog signal to a desired level and a converter means for digitally sampling the amplified analog signal to convert the analog signal to a digitized representation of the analog signal;
        at least one attenuated processing path, each attenuated processing path including attenuation means for attenuating the analog signal, amplifier means for amplifying the attenuated analog signal to a desired level and converter means for digitally sampling the amplified attenuated analog signal to form a digitized representation of the analog signal;
        a logic device receiving each digitized representation of the analog signal from both the at least one unattenuated and at least one attenuated signals, thereby receiving a plurality of digitized signals,
        the logic device comprising means for selecting one digitized signal of the plurality of digitized signals the selected digitized signal being the most linear and having the greatest amplitude of the plurality of digitized signals;
        storage means for storing a plurality of selected digitized signals;
        combining means for combining the stored plurality of digitized signals to form a continuous linear digital waveform; and
    display means for displaying the combined continuous linear digital waveform.

2. The apparatus of claim 1, wherein the combining means is a set of logic circuits configured to convert the plurality of digitized signals to a logarithmic scale to compress the amplitude of the continuous linear digital waveform over a wide dynamic range.

3. The apparatus of claim 2, wherein the analog signal is a low frequency signal and the converter means has a digital sampling rate of about 50 MHz.

4. The apparatus of claim 2, wherein the analog signal is a high frequency signal and the converter means has a digital sampling rate of about 100 MHz.

5. The apparatus of claim 2, wherein the converter means is a 14-bit analog-to-digital signal converter.

6. The apparatus of claim 1, wherein the analog signal is a low frequency signal and the converter means has a digital sampling rate of about 50 MHz.

7. The apparatus of claim 1, wherein the analog signal is a high frequency signal and the converter means has a digital sampling rate of about 100 MHz.

8. The apparatus of claim 1, wherein the converter means is a 14-bit analog-to-digital signal converter.

9. The apparatus of claim 1, wherein the attenuating means of the at least one attenuated path is an attenuator, and each of the attenuated paths has an attenuator of a different attenuation value.

10. The apparatus of claim 9, wherein the different attenuation values are comprised of −6 dB increments.

11. A method for converting an analog signal into a plurality of digital components representing a reflected ultrasonic waveform for testing the physical characteristics of an object, comprising the steps of:

providing a plurality of parallel amplifier paths, each of the paths having an amplifier with a predetermined gain level suitable for a desired predetermined analog output signal level range;

attenuating the analog signal at a plurality of predetermined attenuation levels prior to inputting the analog signal to at least one of the amplifier paths; amplifying the analog signal simultaneously through the plurality of amplifier paths;

converting the amplified analog output signals from each of the plurality of amplifiers to a digital signal;

determining which converted digital signal of the plurality of converted digital signals has a linear response greater than the amplitude of the other converted digital signals;

storing the linear converted digital signal with the greatest amplitude in a digital storage means; combining a plurality of stored digital signals to produce a digital representation of the reflected waveform having a wider dynamic response range than the sum of the plurality of amplifiers; and displaying the combined greatest linear converted digital signals on an output device for analysis of the physical properties and any defects or imperfections of the test object.

12. The method of claim 11 above, also including the step of, inputting the combined linear converted digital signals into a logarithmic conversion means, and displaying the combined greatest linear converted digital signals on an output device for analysis of the physical properties and any defects or imperfections of the test object.

13. A digital log amplifier for processing an ultrasonic analog signal representative of a reflected wave, the amplifier comprising:

at least one unattenuated processing path including amplifier means for amplifying the analog signal to a desired level;

converter means for digitally sampling the amplified analog signal to convert the analog signal to a digitized representation of the analog signal;

at least one attenuation processing path, each attenuation processing path including attenuation means for attenuating the analog signal, amplifier means for amplifying the attenuated analog signal to a desired level; and converter means for digitally sampling the amplified attenuated analog signal to form a digitized representation of the analog signal;

logic circuit means for selecting one digitized signal of the plurality of digitized signals which is linear and which has the greatest amplitude of the plurality of digitized signals;

storage means for storing a plurality of selected digitized signals; and combining means for combining the stored plurality of digitized signals to form a continuous linear digital waveform.

14. The digital log amplifier of claim 13, wherein the combining means is a set of logic circuits configured to convert the plurality of digitized signals to a logarithmic scale to compress the amplitude of the continuous linear digital waveform over a wide dynamic range.

15. The digital log amplifier of claim 14, wherein the analog signal is a low frequency signal and the converter means digital sampling rate is about 50 MHz.

16. The apparatus of claim 14, wherein the analog signal is a high frequency signal and the converter means digital sampling rate is about 100 MHz.

17. The apparatus of claim 14, wherein the converter means is a 14-bit analog-to-digital signal converter.

18. The digital log amplifier of claim 13, wherein the analog signal is a low frequency signal and the converter means digital sampling rate is about 50 MHz.

19. The apparatus of claim 13, wherein the analog signal is a high frequency signal and the converter means digital sampling rate is about 100 MHz.

20. The apparatus of claim 13, wherein the converter means is a 14-bit analog-to-digital signal converter.

21. The apparatus of claim 13, wherein the attenuating means of the at least one attenuated path is an attenuator, and each of the attenuated paths has an attenuator of a different attenuation value.

22. The apparatus of claim 21, wherein the different attenuation values are comprised of −6 dB increments.

* * * * *